US012508149B2

(12) United States Patent
Umemoto et al.

(10) Patent No.: US 12,508,149 B2
(45) Date of Patent: Dec. 30, 2025

(54) NASAL CAVITY INSERTION DEVICE

(71) Applicant: nastent, inc., Tokyo (JP)

(72) Inventors: Tomohiro Umemoto, Tokyo (JP); Takeshi Jibiki, Tokyo (JP)

(73) Assignee: nastent, inc., Tokyo (JP)

( * ) Notice: Subject to any disclaimer, the term of this patent is extended or adjusted under 35 U.S.C. 154(b) by 0 days.

(21) Appl. No.: 18/847,625

(22) PCT Filed: Mar. 18, 2022

(86) PCT No.: PCT/JP2022/012572

§ 371 (c)(1),
(2) Date: Sep. 16, 2024

(87) PCT Pub. No.: WO2023/175887

PCT Pub. Date: Sep. 21, 2023

(65) Prior Publication Data

US 2025/0195254 A1 Jun. 19, 2025

(51) Int. Cl.
*A61F 5/08* (2006.01)
*A61F 5/56* (2006.01)

(52) U.S. Cl.
CPC . *A61F 5/08* (2013.01); *A61F 5/56* (2013.01)

(58) Field of Classification Search
CPC ......... A61F 5/08; A61F 5/56; A61M 16/0461; A61M 16/0666; A61M 2206/14; A61M 2206/16; A61M 2210/0618; A61M 29/00; A61M 15/08; A61M 16/0672; A61M 16/0677
See application file for complete search history.

(56) References Cited

U.S. PATENT DOCUMENTS

2014/0094840 A1 4/2014 Hioki et al.
2021/0169678 A1 6/2021 Sasaki

FOREIGN PATENT DOCUMENTS

JP 2009-285004 A 12/2009
JP 2012-239478 A 12/2012
JP 2019-97904 A 6/2019
WO 2014/163110 A2 10/2014

OTHER PUBLICATIONS

International Search Report [English] for International Application No. PCT/JP2022/012572, mailing date Apr. 26, 2022, 2 pages.
International Search Report for International Application No. PCT/JP2022/012572, mailing date Apr. 26, 2022, 3 pages.

*Primary Examiner* — Victoria Hicks Fisher
(74) *Attorney, Agent, or Firm* — Seed Intellectual Property Law Group LLP

(57) ABSTRACT

A minimally invasive nasal cavity insertion device can be used in either the left or right nasal cavity. A cylindrical tube for insertion into a nasal cavity includes, in a circumferential direction, a first region, a second region opposite the first region, and a pair of left and right connecting regions connecting between the first and second regions. The clipper is connected to a first of the connecting regions. The outer peripheral surface of the tube is provided with a plurality of grooves extending in the circumferential direction, and the plurality of grooves are arranged at intervals in the axial direction. The plurality of grooves include first grooves provided in a first region avoiding at least the second region, and second grooves provided in the second region avoiding at least the first region.

13 Claims, 9 Drawing Sheets

NASAL CAVITY INSERTION DEVICE

BACKGROUND

Technical Field

The present disclosure relates to a nasal cavity insertion device.

Description of the Related Art

Symptoms such as "loud snoring" and "stop breathing during sleep" occur when the upper airway becomes narrow or blocked while sleeping. The present inventors have previously proposed securing an airway during sleep by inserting a soft, tube-shaped nasal cavity insertion device into the nasal cavity, as disclosed in Patent Document 1 below. When the nasal cavity insertion device is inserted through the naris, the tip thereof reaches the uvula, preventing blockage or narrowing of the airway and helping to ensure breathing.

PATENT DOCUMENTS

[Patent Document 1] International Patent Publication No. 2014/163110.

BRIEF SUMMARY

In order to reduce invasiveness to the living body, it is preferable to insert the device alternately into the left and right nasal cavities rather than inserting the device into only one of the left and right nasal cavities. The nasal cavity insertion tube described in Patent Document 1 is gently curved to fit the shape of the left and right nasal cavities. The left and right devices are mirror images of each other, so a device for the right side cannot be inserted into the left nostril, and a device for the left side cannot be inserted into the right nostril. In order to insert the device alternately into the left and right nasal cavities, it is necessary to prepare two different devices, one for the left side and one for the right side.

If the nasal insertion device was designed to be straight and not curved, the device could be used on either the left or right sides. However, devices that are not curved to fit the shape of the nasal cavity tend to create greater resistance when inserted into the nasal cavity, which can cause pain to the user. If the device is made soft so as not to cause pain, the device will be crushed by the uvula, or the like, inhibiting the ability to ensure air passage in the upper airway.

Therefore the present disclosure provides a nasal cavity insertion device that is minimally invasive and can be used in either the left or right nasal cavity.

A nasal cavity insertion device according to a first aspect of the present disclosure includes a cylindrical tube for insertion into a nasal cavity, and a clipper for securing a rear end side of the tube to a bridge of the nose. In the circumferential direction of the tube, the tube includes a first region, a second region opposite the first region, and a pair of left and right connecting regions connecting the first region and the second region. The clipper is connected to a first of the pair of connecting regions. An outer peripheral surface of the tube is provided with a plurality of grooves extending in the circumferential direction of the tube, the plurality of grooves being arranged at intervals in the axial direction of the tube. The plurality of grooves includes first grooves provided in the first region while avoiding at least the second region, and second grooves provided in the second region while avoiding at least the first region.

A nasal cavity insertion device according to a second aspect of the present disclosure includes a cylindrical tube for insertion into a nasal cavity, and a clipper for securing the tube to a bridge of the nose. In the circumferential direction of the tube, the tube includes a first region, a second region opposite the first region, and a pair of left and right connecting regions connecting the first region and the second region. The clipper is connected to a first of the pair of connecting regions. The first and second regions are formed so that wall thicknesses thereof in the radial direction of the tube are greater than the wall thicknesses of the pair of connecting regions.

According to these aspects, by forming grooves or adjusting the wall thickness of the tube, a tube can be configured that is easy to bend and difficult to crush, thereby providing a nasal cavity insertion device that is minimally invasive and can be used in either the left or right nasal cavity.

In the aspect described above, the tube preferably has a straight central axis in an initial, undeformed state.

According to this aspect, the tube can be easily bent in either direction, making the tube suitable for use as a device for both left and right sides.

In the aspect described above, the first and second grooves are preferably formed in positions that do not overlap with each other in the radial direction of the tube and in the direction in which the first region and the second region face each other.

According to this aspect, even if the tube is bent at the first and second grooves, the tube will not be crushed at the same position from both above and below the first and second regions, making it easier to ensure air passage.

In the aspect described above, the first grooves may be provided so as to avoid the second region and the pair of connecting regions, and the second grooves may be provided so as to avoid the first region and the pair of connecting regions.

According to this aspect, since there is a pair of connecting regions in which neither the first groove nor the second groove is provided, a tube having excellent tensile strength can be formed.

In the aspect described above, the length of each of the plurality of grooves in the circumferential direction of the tube may be 1200 or more to 1500 or less in the circumferential direction of the tube.

According to this aspect, the flexibility of the tube can be adjusted by using grooves of sufficient length.

In the aspect described above, the first grooves may be provided across the first region and the pair of connecting regions. The second groove may be provided across the second region and the pair of connecting regions.

According to this aspect, the flexibility of the tube can be significantly changed by the grooves having a length exceeding 180°. Even tubes with hard rubber hardness can be easily bent and adjusted.

In the aspect described above, in the axial direction of the tube, the tube may have a first portion including a rear end and a second portion including a front end opposite the rear end. The second portion may have an outer peripheral surface provided with a plurality of third grooves extending around the full circumference, across the second region and the pair of connecting regions.

According to this aspect, the third grooves can be provided to make the second portion softer than the first portion. The hardness of the tube can be optimally adjusted for each portion.

In the aspect described above, the depth of each of the plurality of grooves is preferably 45% or more and 65% or less of the wall thickness of the tube.

According to this aspect, both the tensile strength and hardness of the tube can be adjusted.

In the aspect described above, the tube preferably has a front end opposite to the rear end, and the tip part including the front end and a portion in the vicinity of the front end has a tapered shape in which the outer diameter decreases toward the front end.

According to this aspect, even if the front end of the tube comes into contact with the nasal cavity or pharynx, the tube is unlikely to damage the nasal cavity or pharynx, so that the invasiveness can be suppressed even if the nasal cavity insertion device is used repeatedly.

In the aspect described above, the clipper is preferably a resin spring made from a resin material.

According to this aspect, the nasal cavity insertion device can be made entirely of resin material. If a metal spring is included, sterilization by heating in a microwave oven or the like is not feasible, but with this configuration, sterilization by heating in a microwave oven is feasible. This allows for more hygienic use of the device.

According to the present disclosure, a nasal cavity insertion device which is minimally invasive and can be used in either the left or right nasal cavity can be provided.

DESCRIPTION OF THE PREFERRED EMBODIMENTS

Figure 1:
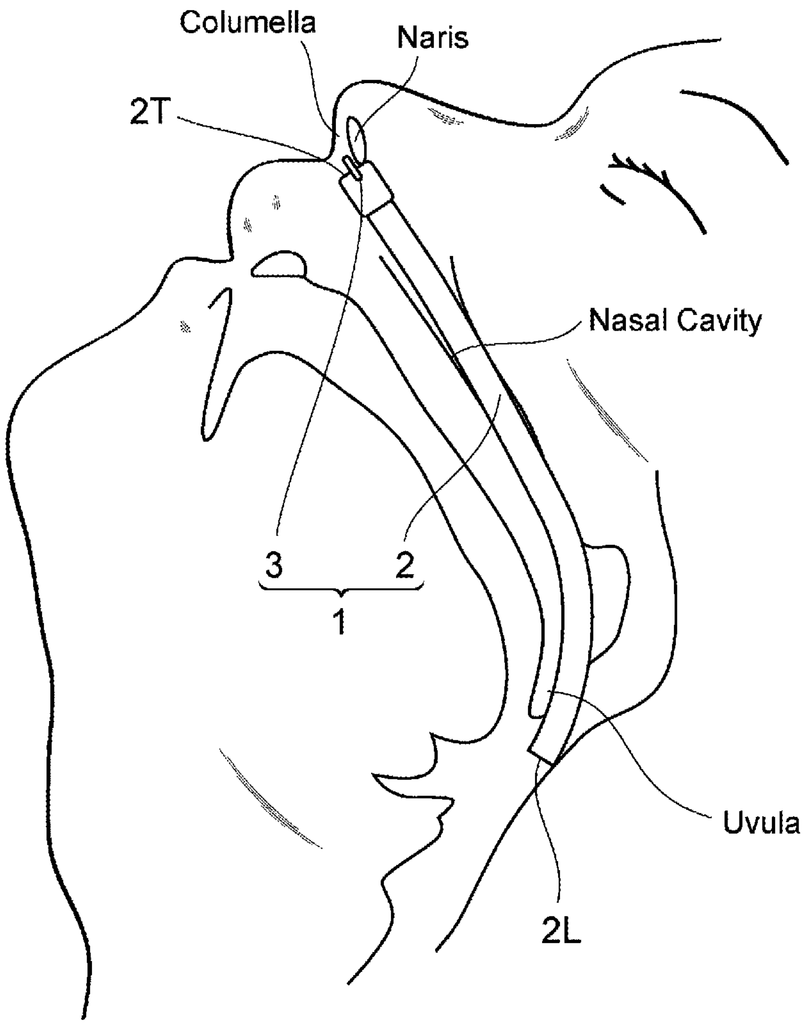
FIG. 1 shows a perspective view depicting how to use a nasal cavity insertion device according to embodiments of the present disclosure.

A preferred embodiment of the present disclosure will be described below with reference to the attached drawings. Note that in each diagram, the same reference numerals designate identical or similar configurations. FIG. 1 shows a perspective view depicting how to use a nasal cavity insertion device 1 according to each embodiment of the present disclosure. As depicted in FIG. 1, a nasal cavity insertion device 1 is inserted into the nasal cavity to secure an airway.

The nasal cavity insertion device 1 includes a flexible tube 2 and a clipper 3 connected to a rear end 2T of the tube 2. The tube 2 is formed in a cylindrical shape that is slightly longer than the distance from the naris to the uvula of the user. The length of the tube 2 from the rear end 2T to the front end 2L is, for example, about 120 mm to 160 mm, and varies depending on the height and body type of the user.

The clipper 3 secures the rear end 2T of the tube 2 to the columella to prevent the tube 2 from falling into the body of the user. The clipper is, for example, formed from a material having spring elasticity and has a hook shape. Because the nasal cavity insertion device 1 can be sterilized by heating in a microwave oven, the clipper 3 is preferably a resin spring formed from a resin material such as polycarbonate resin. Note that the material of the clipper 3 is not limited to a resin material, but may be a metal material such as stainless steel.

Embodiment 1

Figure 2:
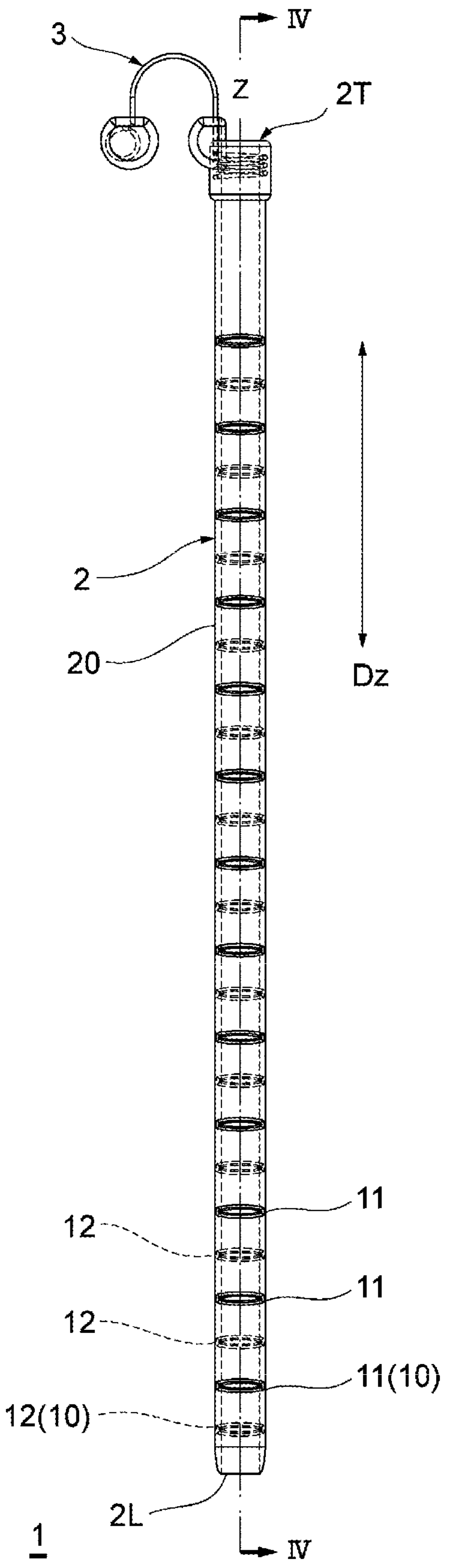
FIG. 2 shows a plan view depicting an example of the nasal cavity insertion device according to Embodiment 1 of the present disclosure.

FIG. 2 shows a plan view depicting an example of the nasal cavity insertion device 1 according to Embodiment 1 of the present disclosure. As depicted in FIG. 2, the tube 2 preferably has a central axis Z that is straight in an initial, undeformed state. Note that the tube 2 may be slightly curved so long as there is only a slight discomfort to the user when the tube is inserted into the nasal cavity.

Figure 3:
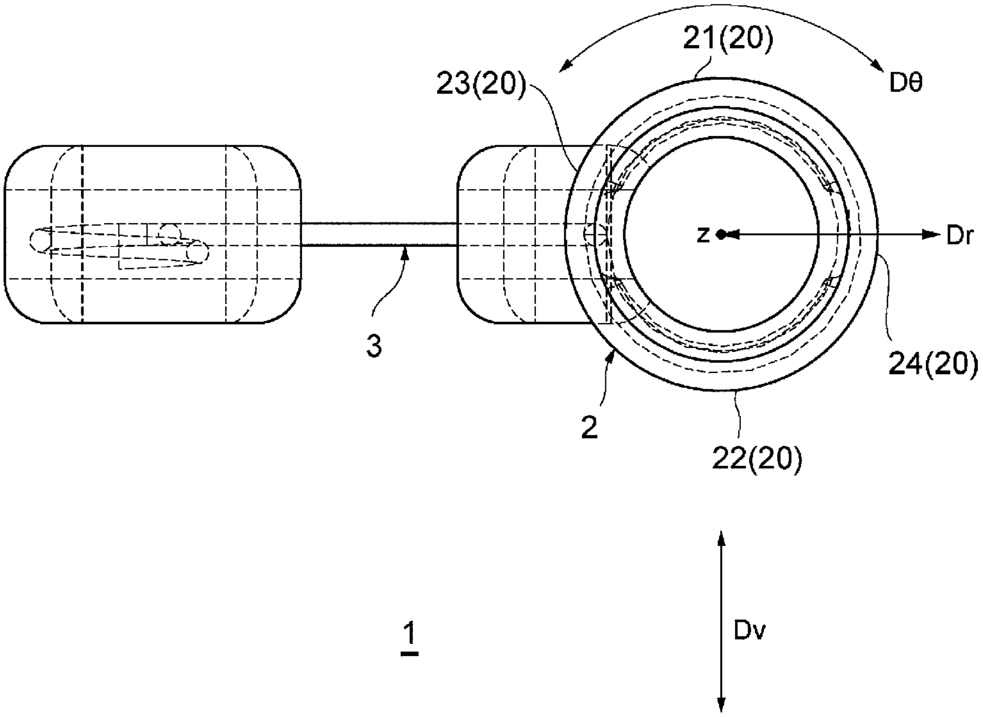
FIG. 3 shows a front view of the nasal cavity insertion device depicted in FIG. 2 as viewed along the axial direction.

FIG. 3 shows a front view of the nasal cavity insertion device 1 depicted in FIG. 2 as viewed along the axial direction Dz from the front end 2L of the tube 2 to the rear end 2T. As depicted in FIG. 3, the outer peripheral surface 20 of the cylindrical tube 2 is divided into four parts in the circumferential direction Dθ of the tube 2, and includes a first region 21, a second region 22 that is 180° opposite to the first region 21, and a pair of connecting regions 23, 24 that connect the first region 21 and the second region 22.

The clipper 3 is connected to connecting region 23, which is a first of the pair of left and right connecting regions 23 and 24. In the example depicted, the nasal insertion device 1 is oriented to be inserted into the right nostril, and the first connecting region 23 to which the clipper 3 is connected is on the left surface. In this case, the first region 21 becomes the upper surface, the second region 22 becomes the lower surface, and a second connecting region 24 becomes the right surface.

Although not depicted in the drawings, in the orientation in which the nasal cavity insertion device 1 is inserted into the left nostril, the first connecting region 23 to which the clipper 3 is connected is on the right surface. In this case, the first region 21 becomes the lower surface, the second region 22 becomes the upper surface, and the second connecting region 24 becomes the left surface.

Figure 4:
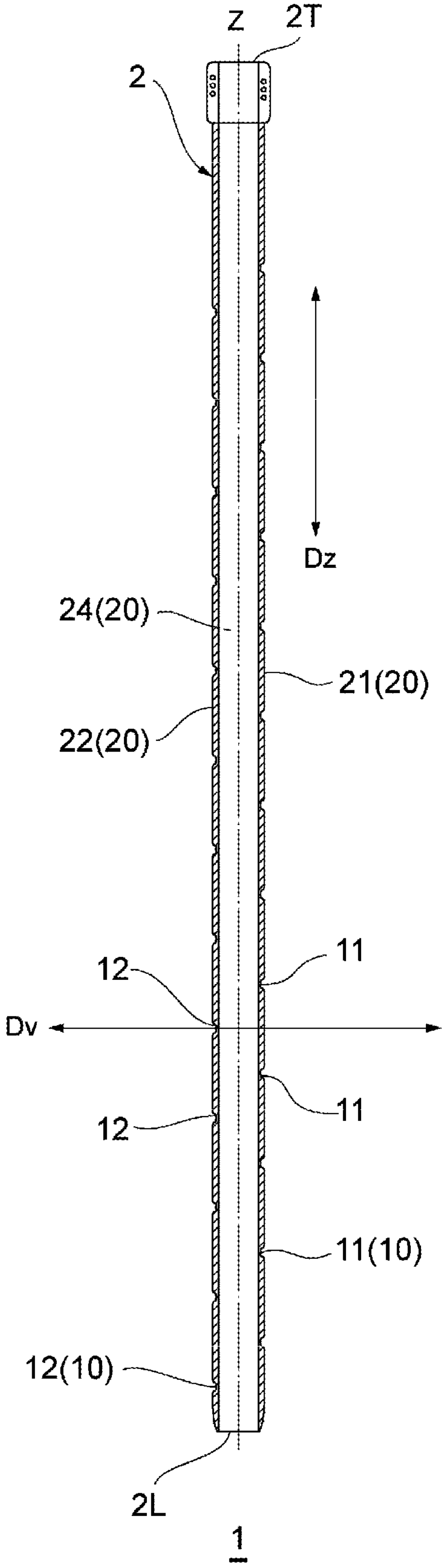
FIG. 4 shows a cross-sectional view taken along the line IV-IV depicted in FIG. 2.

FIG. 4 shows a cross-sectional view taken along the line IV-IV depicted in FIG. 2. As depicted in FIGS. 2 and 4, the outer peripheral surface 20 of the tube 2 is provided with a plurality of grooves 10 extending in the circumferential direction Dθ of the tube 2. The plurality of grooves 10 are arranged at intervals in the axial direction Dz of the tube 2. The depth of each of the grooves 10 is, for example, 45% or more to 65% or less of the wall thickness of the tube 2, and preferably 50% or more to 60% or less of the wall thickness of the tube 2. In the example depicted, the depth of the grooves 10 is 55% of the wall thickness of the tube 2.

The plurality of grooves 10 includes a plurality of first grooves 11 and a plurality of second grooves 12. As depicted in FIG. 2 and FIG. 4, the plurality of first grooves 11 are provided in the first region 21 so as to avoid the pair of connecting regions 23, 24. The plurality of second grooves 12 are provided in the second region 22 so as to avoid the pair of connecting regions 23, 24. In other words, the first grooves 11 are provided in the first region 21 while avoiding at least the second region 22. The second grooves 12 are provided in the second region 22 while avoiding at least the first region 21.

As depicted in FIG. 4, the first grooves 11 and the second grooves 12 are formed in a radial direction Dθ of the tube 2 and at a position where they do not overlap with each other in a direction Dv (for example, the vertical direction as viewed by the user) in which the first region 21 and the second region 22 are opposed.

In the example depicted, a plurality of first grooves 11 are provided at intervals of 10 mm in the axial direction Dz of the tube 2. Similarly, a plurality of second grooves 12 are provided at intervals of 10 mm. The first grooves 11 and the second grooves 12 are formed at positions offset from each other by 5 mm in the axial direction Dz of the tube 2.

The length of each of the first grooves 11 in the circumferential direction Dθ of the tube 2 is, for example, 900 or more to 150° or less, and preferably 1200 or more to 150° or less. In the example depicted in FIG. 2, the length of each of the first grooves 11 is formed to be 135° (3/8 of the entire circumference) in the circumferential direction Dθ of the tube 2. The length of each of the second grooves 12 is formed to be substantially the same as the length of each of the first grooves 11.

Figure 5:
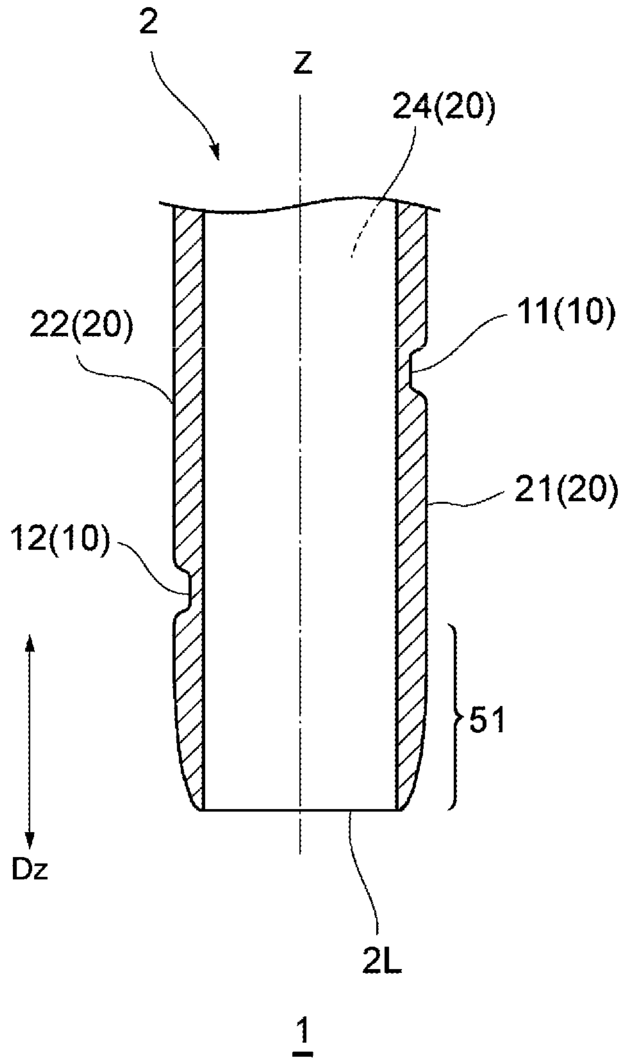
FIG. 5 shows an enlarged cross-sectional view depicting a tip part of the nasal cavity insertion device depicted in FIG. 4.

FIG. 5 shows an enlarged cross-sectional view depicting a tip part 51 of the nasal cavity insertion device depicted in FIG. 4. As depicted in FIG. 5, a tip part 51 including the tip 2L of the tube 2 and a portion in the vicinity thereof is formed in a tapered shape such that the outer diameter becomes smaller toward the tip 2L. The tip part 51 is a part that is, for example, 2 mm or more and 5 mm or less from the front end 2L.

The tapered shape may be, for example, a streamlined shape in which the curvature of the cross section changes continuously, a fillet (rounded chamfer) in which the curvature of the cross section does not change, or a taper in which the cross section is a straight conical surface. Preferably the shape is streamlined or a fillet. In the example depicted, the tip part 51 including the portion 3 mm from the front end 2L is formed in a streamlined shape.

According to the nasal cavity insertion device 1 of the Embodiment 1 configured as described above, the tube 2 can be easily bent at the grooves 10, and therefore the user feels only slight discomfort when inserting the nasal cavity insertion device 1 into the nasal cavity. Since it is not necessary to make the rubber hardness of the tube 2 extremely soft, the tube 2 is unlikely to be crushed by the uvula or the like. Therefore, a nasal cavity insertion device 1 that is minimally invasive and can be used in either the left or right nasal cavity can be provided.

In the facing direction Dv in which the first region 21 and the second region 22 oppose each other, the first grooves 11 and the second grooves 12 are formed at offset positions so as not to overlap with each other, so that the tube 2 is less likely to be crushed by the uvula, or the like. This ensures proper air flow. Since the tip part 51 of the tube 2 is formed in a tapered shape, even if the front end 2L of the tube 2 contacts the nasal cavity or pharynx, injury to the nasal cavity or pharynx is unlikely. Even if the nasal cavity insertion device 1 is used repeatedly, the invasiveness can be reduced.

Embodiment 2

Figure 6:
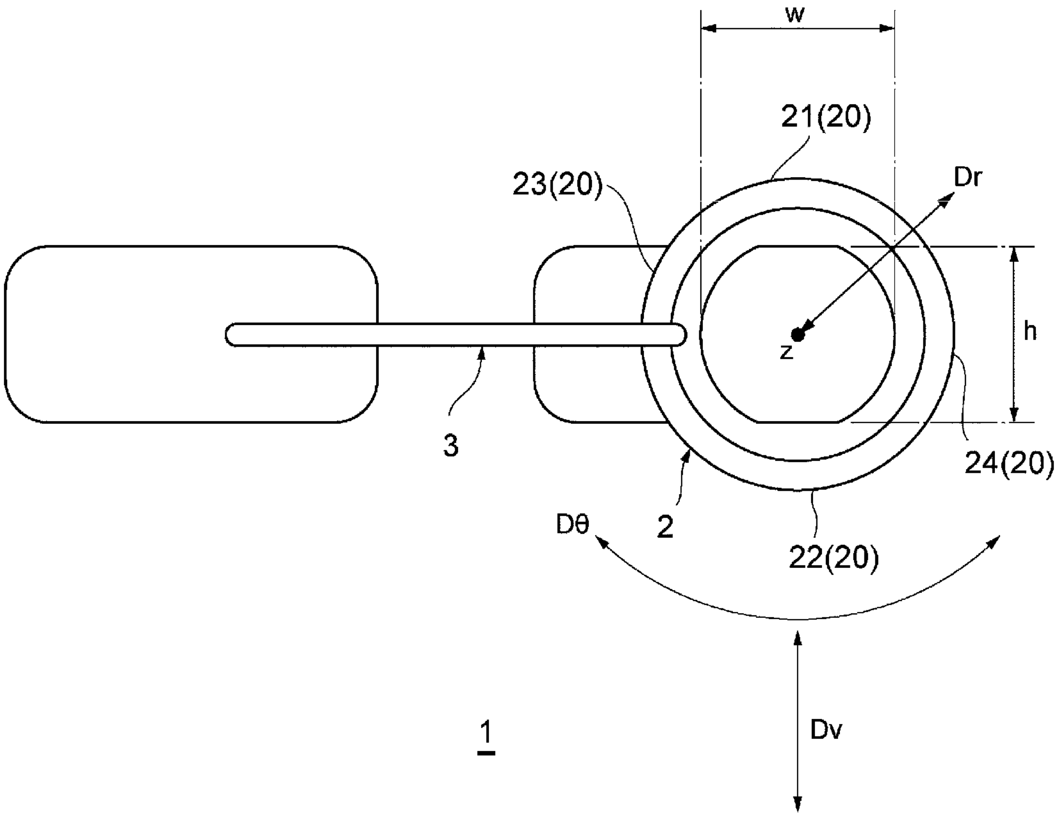
FIG. 6 shows a front view depicting an example of the nasal cavity insertion device according to Embodiment 2 of the present disclosure.

In the Embodiment 2 to Embodiment 5, descriptions of matters common to Embodiment 1 will be omitted, and only the differences will be described. FIG. 6 shows a front view depicting an example of the nasal cavity insertion device 1 according to Embodiment 2 of the present disclosure. As depicted in FIG. 6, the nasal cavity insertion device 1 of Embodiment 2 differs from that of Embodiment 1 in that the thicknesses of the first and second regions 21, 22 are formed larger than the thicknesses of the pair of connecting regions 23, 24.

In the example indicated, the outer circumference of the tube 2 is a perfect circle, and in the internal space of the tube 2, the distance between the first and second regions 21, 22, in other words, the height h of the internal space, is smaller than the distance between the pair of connecting regions 23, 24, in other words, the width w of the internal space. Although not depicted, similar to Embodiment 1, the first grooves 11 are provided in the first region 21 of the tube 2 so as to avoid the pair of connecting regions 23 and 24. The second grooves 12 are provided in the second region 22 so as to avoid the pair of connecting regions 23 and 24.

According to Embodiment 2 configured as described above, the tube 2 is formed thick in the first and second regions 21, 22, so that the internal space of the tube 2 is less likely to collapse even if the uvula or the like comes into contact the first or second region 21, 22. Since the grooves 10 are provided in the first and second regions 21, 22 which are formed thick, the tube 2 is not excessively rigid and can be bent. Similar to Embodiment 1, a nasal cavity insertion device 1 that is minimally invasive and can be used in either the left or right nasal cavity can be provided.

Embodiment 3

Figure 7:
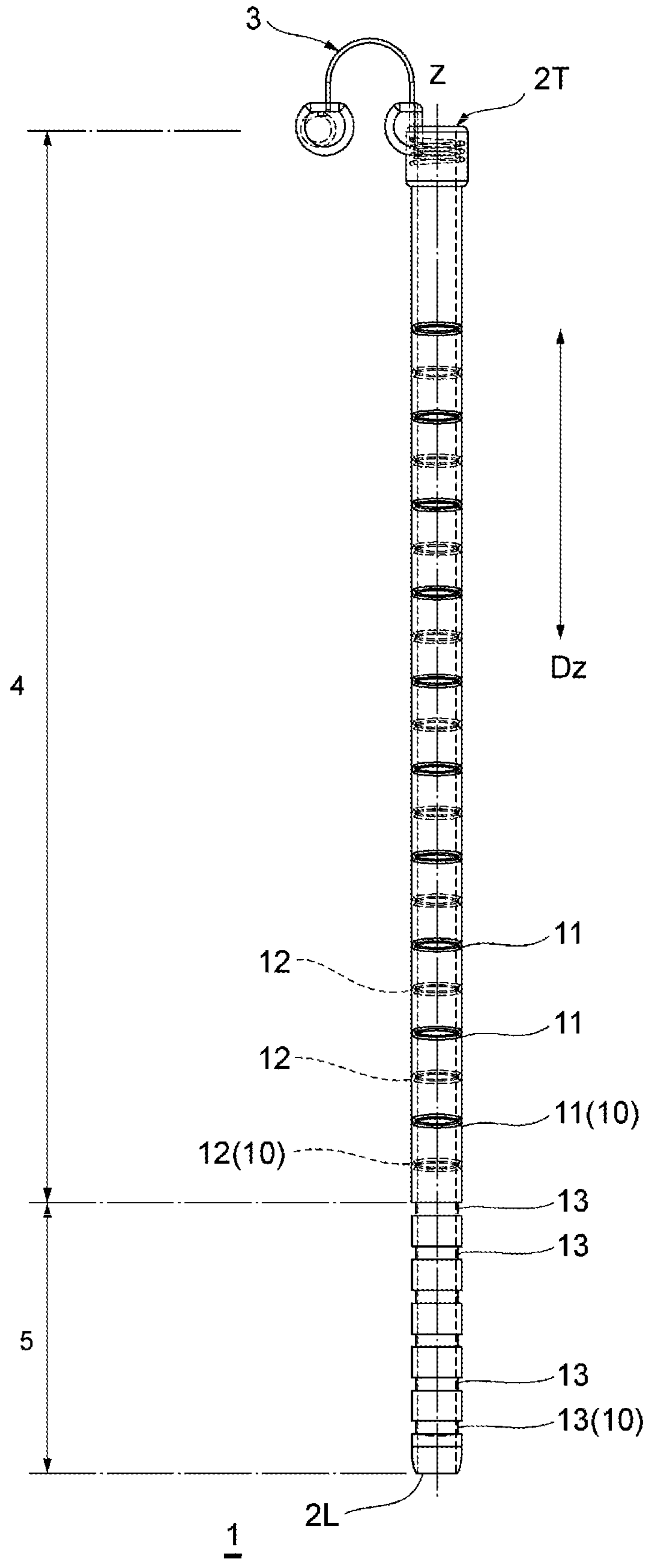
FIG. 7 shows a plan view depicting an example of the nasal cavity insertion device according to Embodiment 3 of the present disclosure.

FIG. 7 shows a plan view depicting an example of the nasal cavity insertion device 1 according to Embodiment 3 of the present disclosure. As depicted in FIG. 7, the nasal insertion device 1 of Embodiment 3 differs from Embodiment 1 in that in addition to the first grooves 11 provided in the first region 21 while avoiding the pair of connecting regions 23, 24 and the second grooves 12 provided in the second region 22 while avoiding the pair of connecting regions 23, 24, a plurality of third grooves 13 extending 360° around the entire circumference throughout the first region 21, the second region 22, and the pair of connecting regions 23, 24 are provided on the tube 2.

The tube 2 according to Embodiment 3 has, in the axial direction Dz of the tube 2, a first portion 4 including a rear end 2T (depicted in FIG. 1) and a second portion 5 including the front end 2L. The second portion 5 is a portion that ensures air passage in the vicinity of the uvula, and is shorter than the first portion 4. The first portion 4 is a portion that ensures air passage within the nasal cavity, and is the remaining portion of the tube 2 excluding the second portion 5.

The first portion 4 is provided with the plurality of first and second grooves 11, 12. The second portion 5 is provided with the third grooves 13. In the example depicted, the second portion 5 is defined as a portion extending 30 mm from the front end 2L of the tube 2, and a plurality of third grooves 13 are provided in the second portion 5 at intervals of 5 mm.

The first portion 4 has a gentler curve than the second portion 5. Since the first and second grooves 11, 12 of Embodiment 4 are provided in the first portion 4, the length in the circumferential direction Dθ of the tube 2 may be shorter than that of the first and second grooves 11, 12 of Embodiment 1. In the example depicted, the length of each of the first and second grooves 11, 12 is 90°.

According to the nasal cavity insertion device 1 of Embodiment 3 configured as described above, providing of the third grooves 13 enables the second portion 5 to be softer than the first portion 4. Since the hardness of the tube 2 can be optimally adjusted for each portion, a nasal cavity insertion device 1 that is minimally invasive and can be used in either the left or right nasal cavity can be provided.

Embodiment 4

Figure 8:
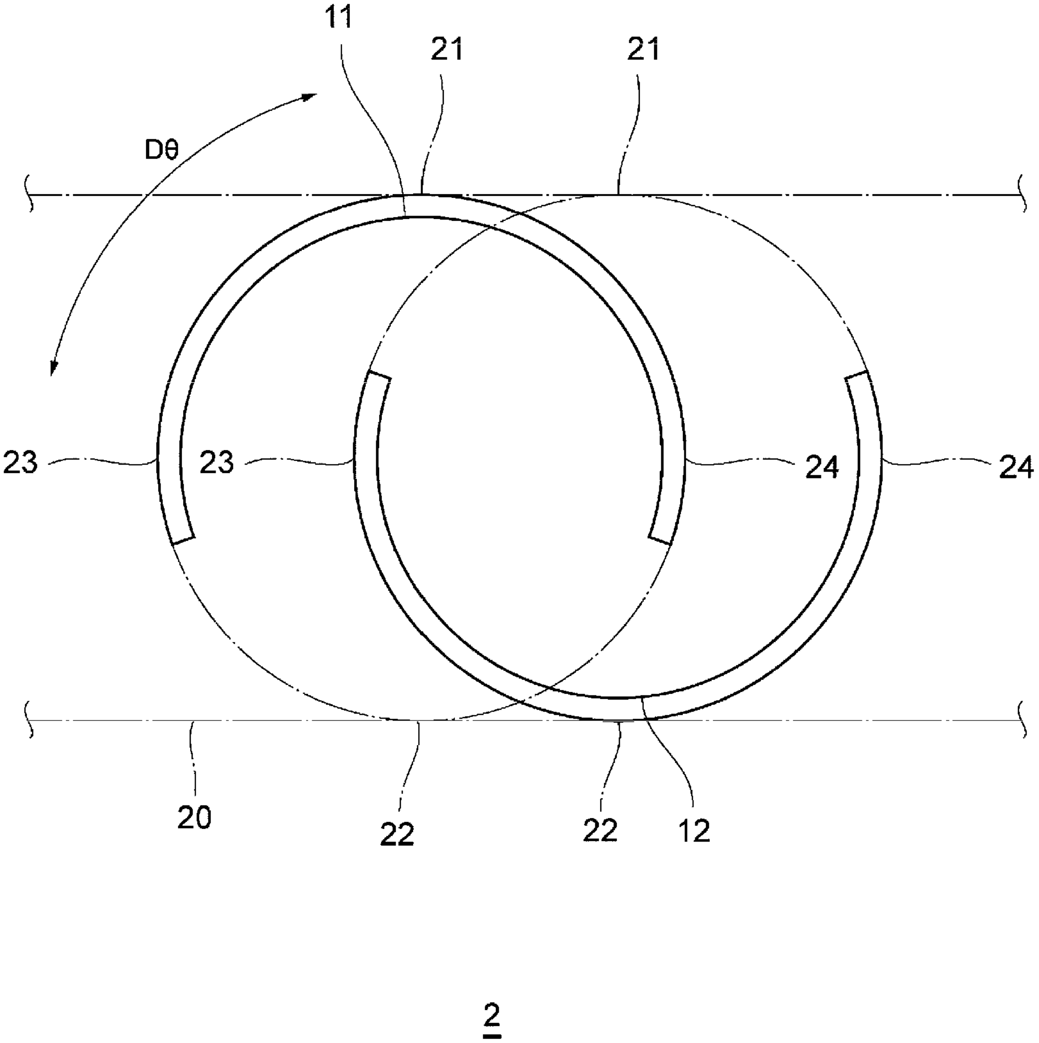
FIG. 8 shows a cross-sectional view that illustrates an example of a nasal cavity insertion device according to Embodiment 4 of the present disclosure.

FIG. 8 shows a cross-sectional view that illustrates an example of a nasal cavity insertion device 1 according to Embodiment 4 of the present disclosure. As depicted in FIG. 8, the nasal cavity insertion device 1 of Embodiment 4 differs from that of Embodiment 1 in that grooves 10 having a length exceeding 180° in the circumferential direction θ of the tube 2 are provided. In the example depicted, the length of each of the first and second grooves 11, 12 is 225° (5/8 of the entire circumference).

As depicted in FIG. 8, the first grooves 11 are provided across the first region 21 and the pair of connecting regions 23 and 24, while avoiding the second region 22. The second grooves 12 are provided across the second region 22 and the pair of connecting regions 23 and 24, while avoiding the first region 21. As in Embodiment 1, the first grooves 11 are provided in the first region 21 while avoiding at least the second region 22. The second grooves 12 are provided in the second region 22 while avoiding at least the first region 21.

In the nasal cavity insertion device 1 of Embodiment 4 configured as described above, by providing the grooves 10 that are longer than those in Embodiment 1, the flexibility of the tube 2 can be changed dramatically. Since even the tube 2 having a hard rubber hardness can be easily bent and adjusted, a nasal cavity insertion device 1 that is minimally invasive and can be used in either the left or right nasal cavity can be provided.

Embodiment 5

Figure 9:
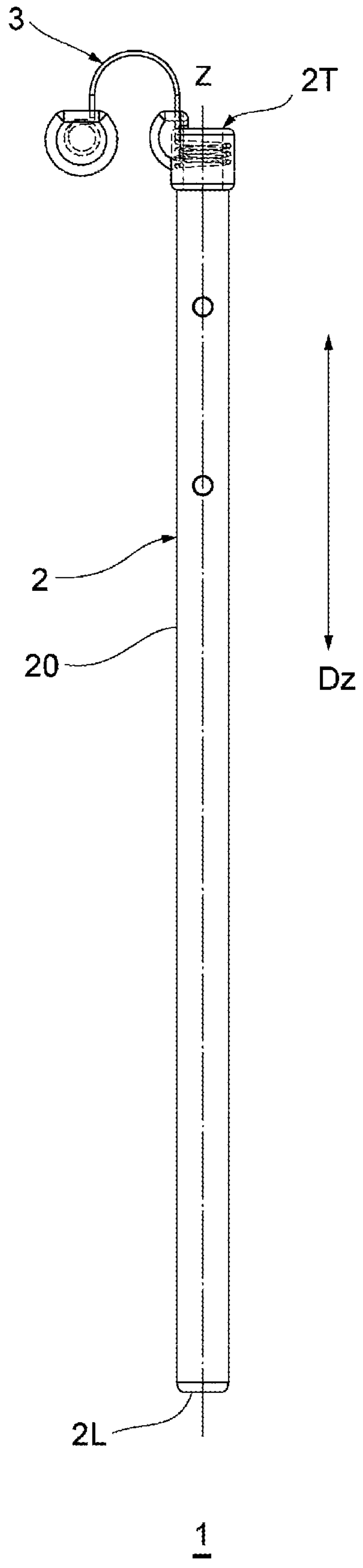
FIG. 9 shows a plan view depicting an example of the nasal cavity insertion device according to Embodiment 5 of the present disclosure.

FIG. 9 shows a plan view depicting an example of the nasal cavity insertion device 1 according to Embodiment 5 of the present disclosure. As depicted in FIG. 9, the nasal cavity insertion device 1 of Embodiment 5 differs from Embodiment 1 in that the grooves 10 are not formed. In the nasal cavity insertion device 1 of Embodiment 5, similar to Embodiment 2, the wall thicknesses of the first and second regions 21 and 22 are formed to be greater than the wall thicknesses of the pair of connecting regions 23 and 24.

According to the nasal insertion device 1 of Embodiment 5 configured as described above, the tube 2 is formed to be thick in the first and second regions 21, 22. Therefore, even if the uvula or the like comes into contact with the first or second region 21, 22, the internal space of the tube 2 is unlikely to be crushed. Since the rubber hardness can be made softer than when a tube 2 with a uniform thickness is used, a nasal cavity insertion device 1 that is minimally invasive and that can be used in either the left or right nasal cavity can be provided.

The embodiments described above are for ease of understanding of the present disclosure and are not intended to be construed as limiting the present disclosure. Elements included in the embodiment, as well as arrangements, materials, conditions, shapes, sizes, and the like thereof, are not limited to those exemplified, but rather can be appropriately changed. In addition, the configurations shown in the various embodiments can be partially replaced or combined with each other.

REFERENCE NUMERALS

- 1 Nasal cavity insertion device,
- 2 Tube
- 2L Front end
- 2T Rear end
- 3 Clipper
- 4 First portion
- 5 Second portion
- 10 Grooves
- 11 First groove
- 12 Second grooves
- 13 Third grooves
- 20 Outer peripheral surface
- 21 First region
- 22 Second region
- 23, 24 Connecting regions
- 51 Tip part
- Dr Radial direction
- Dv Facing direction
- Dz Axial direction
- Dθ Circumferential direction
- h Height
- w Width

The invention claimed is:

1. A nasal cavity insertion device, comprising:

a cylindrical tube for insertion into a nasal cavity of a nose; and a clipper for securing a rear end of the cylindrical tube to a bridge of the nose, wherein:

the cylindrical tube includes a first region and a second region opposite the first region in a circumferential direction of the cylindrical tube, and a pair of connecting regions including left and right connecting regions that connect between the first region and the second region, the clipper is connected to a first connecting region of the pair of connecting regions, a plurality of grooves extending in the circumferential direction of the cylindrical tube are provided on the outer peripheral surface of the cylindrical tube and the plurality of grooves are spaced at intervals along the axial direction of the cylindrical tube, and the plurality of grooves includes first grooves provided in the first region at least avoiding the second region and second grooves provided in the second region at least avoiding the first region.

2. The nasal cavity insertion device according to claim 1, wherein the cylindrical tube has a straight central axis in an initial undeformed state.

3. The nasal cavity insertion device according to claim 1, wherein the first grooves and the second grooves are formed in a radial direction of the cylindrical tube in positions so as to not overlap with each in a direction where the first region and the second region face each other.

4. The nasal cavity insertion device according to claim 1, wherein the first grooves are provided so as to avoid the second region and the pair of connecting regions, and the second grooves are provided so as to avoid the first region and the pair of connecting regions.

5. The nasal cavity insertion device according to claim 4, wherein the length of the first grooves and the second grooves in the circumferential direction of the cylindrical tube is 120° or more to 150° or less of the circumferential direction of the cylindrical tube.

6. The nasal cavity insertion device according to claim 1, wherein the first grooves are provided across the first region and the pair of connecting regions, and the second grooves are provided across the second region and the pair of connecting regions.

7. The nasal cavity insertion device according to claim 1, wherein;

in the axial direction of the cylindrica tube, the cylindrical tube includes a first portion including the rear end and a second portion including a front end on the opposite side from the rear end, and a plurality of third grooves extending the full circumference of the cylindrical tube are provided on the outer peripheral surface of the second portion across the first region, the second region, and the pair of connecting regions.

8. The nasal cavity insertion device according to claim 1, wherein the depth of each of the plurality of grooves is 45% or more to 65% or less of the wall thickness of the cylindrical tube.

9. A nasal cavity insertion device, comprising:

a cylindrical tube for insertion into a nasal cavity of a nose; and a clipper for securing the cylindrical tube to a bridge of the nose;

wherein:

in the circumferential direction of the cylindrical tube, the cylindrical tube includes a first region, a second region on the opposite side from the first region, and a pair of connecting regions including left and right connecting regions connecting between the first region and the second region, the clipper is connected to a first connecting region of the pair of connecting regions, and the wall thickness in the radial direction of the cylindrical tube in the first region and the second region is formed thicker than that for the pair of connecting regions and wherein: a plurality of grooves extending in the circumferential direction of the cylindrical tube are provided on the outer peripheral surface of the cylindrical tube and the plurality of grooves are spaced at intervals along the axial direction of the cylindrical tube, and the plurality of grooves includes first grooves provided in the first region at least avoiding the second region, and second grooves provided in the second region at least avoiding the first region.

10. The nasal cavity insertion device according to claim 1, wherein the cylindrical tube includes a front end opposite the rear end, and a tip part including the front end and a portion near the front end has a tapered shape in which the outer diameter of the cylindrical tube becomes smaller towards the front end.

11. The nasal cavity insertion device according to claim 1, wherein the clipper is a resin spring formed from resin material.

12. The nasal cavity insertion device according to claim 9, wherein the cylindrical tube includes a front end opposite a rear end, and a tip part including the front end and a portion near the front end has a tapered shape in which the outer diameter of the cylindrical tube becomes smaller towards the front end.

13. The nasal cavity insertion device according to claim 9, wherein the clipper is a resin spring formed from resin material.

* * * * *